(12) United States Patent
Guerra et al.

(10) Patent No.: US 12,257,359 B1
(45) Date of Patent: Mar. 25, 2025

(54) SYSTEMS AND METHODS FOR SANITIZED TRANSACTIONS WITH AUTOMATIC TELLER MACHINE

(71) Applicant: United Services Automobile Association (USAA), San Antonio, TX (US)

(72) Inventors: Oscar Guerra, San Antonio, TX (US); Gregory David Hansen, San Antonio, TX (US); Anto Chirayil Thomas, Coppell, TX (US)

(73) Assignee: United Services Automobile Association (USAA), San Antonio, TX (US)

( * ) Notice: Subject to any disclaimer, the term of this patent is extended or adjusted under 35 U.S.C. 154(b) by 1061 days.

(21) Appl. No.: 17/008,374

(22) Filed: Aug. 31, 2020

(51) Int. Cl.
| | |
|---|---|
| G06Q 20/10 | (2012.01) |
| A61L 2/10 | (2006.01) |
| A61L 2/18 | (2006.01) |
| A61L 2/26 | (2006.01) |
| G06Q 20/20 | (2012.01) |
| G07D 11/23 | (2019.01) |
| G07D 11/50 | (2019.01) |
| G07F 19/00 | (2006.01) |
| G06F 3/0488 | (2022.01) |

(52) U.S. Cl.
CPC ....... *A61L 2/26* (2013.01); *A61L 2/10* (2013.01); *A61L 2/18* (2013.01); *G06Q 20/1085* (2013.01); *G06Q 20/203* (2013.01); *G07D 11/23* (2019.01); *G07D 11/50* (2019.01); *G07F 19/203* (2013.01); *A61L 2202/11* (2013.01); *A61L 2202/121* (2013.01); *A61L 2202/14* (2013.01); *A61L 2202/181* (2013.01); *G06F 3/0488* (2013.01); *G07D 2211/00* (2013.01)

(58) Field of Classification Search
None
See application file for complete search history.

(56) References Cited

U.S. PATENT DOCUMENTS

| | | | | | |
|---|---|---|---|---|---|
| 4,201,131 | A | * | 5/1980 | Miyagawa | G06M 9/02 101/4 |
| 5,563,394 | A | * | 10/1996 | Kako | A61L 2/04 902/12 |
| 10,540,644 | B1 | * | 1/2020 | Walker | G07F 19/203 |

OTHER PUBLICATIONS

DeRidder, Philippe, et al.; Strategy Report, BoardofInnovation.com; "The winners of the Low Touch Economy", 104 pages, 2020.

* cited by examiner

*Primary Examiner* — Edwyn Labaze
*Assistant Examiner* — April A Taylor
(74) *Attorney, Agent, or Firm* — Fletcher Yoder, P.C.

(57) ABSTRACT

An automated teller system is provided that includes a user interface configured to receive user input, a bill counter configured to assemble cash, and a sanitizer configured to receive the cash in a sanitized condition and dispense the cash in the sanitized condition via an access port. The automated teller system also includes one or more processors and memory storing machine-readable instructions that, when executed by the one or more processors, are configured to cause the one or more processors to control the bill counter to assemble the cash based on a withdrawal request, the withdrawal request received as the user input via the user input, to control sanitization of the cash by the sanitizer to provide the cash in the sanitized condition and to control the cash dispenser to dispense the cash in the sanitized condition via the access port.

19 Claims, 6 Drawing Sheets

SYSTEMS AND METHODS FOR SANITIZED TRANSACTIONS WITH AUTOMATIC TELLER MACHINE

BACKGROUND

This section is intended to introduce the reader to various aspects of art that may be related to various aspects of the present techniques, which are described and/or claimed below. This discussion is believed to be helpful in providing the reader with background information to facilitate a better understanding of the various aspects of the present disclosure. Accordingly, it should be noted that these statements are to be read in this light, and not as admissions of prior art.

Automatic teller machines (ATMs) are an integral part of how individuals conduct personal finance. Numerous individuals utilize each ATM each day. People's hands touch the screen and keypad. The cash being dispensed from the ATM may have changed hands numerous times. Thus, it is now recognized that each ATM can be a source for spreading germs and contagions between numerous individuals.

SUMMARY

Certain embodiments commensurate in scope with the present disclosure are summarized below. These embodiments are not intended to limit the scope of the disclosure, but rather these embodiments are intended only to provide a brief summary of possible forms of present embodiments. Indeed, present embodiments may encompass a variety of forms that may be similar to or different from the embodiments set forth below.

In an embodiment, an automated teller system includes a user interface configured to receive user input, a bill counter configured to assemble cash, and a sanitizer configured to receive the cash in a sanitized condition and dispense the cash in the sanitized condition via an access port. The automated teller system also includes one or more processors and memory storing machine-readable instructions that, when executed by the one or more processors, are configured to cause the one or more processors to control the bill counter to assemble the cash based on a withdrawal request, the withdrawal request received as the user input via the user input. The instructions, when executed by the one or more processors, are configured to cause the one or more processors to control sanitization of the cash by the sanitizer to provide the cash in the sanitized condition and to control the cash dispenser to dispense the cash in the sanitized condition via the access port.

In an embodiment, a method for dispensing cash from an ATM is provided. The method includes receiving, a user interface of the ATM, a request for a cash withdrawal from a user. The method also includes sanitizing the cash via a sanitizer within a housing of the ATM. The method further includes providing the sanitized cash to the user via a dispenser of the ATM.

In an embodiment, an ATM is provided. The ATM includes a user input device configured to enable a user to request a cash withdrawal. The ATM also includes a sanitization system configured to sanitize cash and to package the sanitized cash within a package prior to providing the cash to the user, and the sanitization system is configured to sanitize the user input device after providing the cash to the user.

BRIEF DESCRIPTION OF THE DRAWINGS

These and other features, aspects, and advantages of the present disclosure will become better understood when the following detailed description is read with reference to the accompanying drawings in which like characters represent like parts throughout the drawings, wherein.

DETAILED DESCRIPTION

The present disclosure generally relates to systems and methods for conducting financial transactions in a sanitary manner. More specifically, the present disclosure relates to dispensing sanitized cash from an automatic teller machine (ATM) to users.

One or more specific embodiments will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present disclosure, the articles "a," "an," and "the" are intended to mean that there are one or more of the elements. The terms "comprising," "including," and "having" are intended to be inclusive and mean that there may be additional elements other than the listed elements. Additionally, it should be understood that references to "one embodiment" or "an embodiment" of the present disclosure are not intended to be interpreted as excluding the existence of additional embodiments that also incorporate the recited features.

Embodiments of the present disclosure are directed to systems and methods for conducting financial transactions in a sanitary manner. In particular, an automated teller machine (ATM) is disclosed that dispenses sanitized and/or sanitarily packaged cash to a user. For example, upon a request for cash withdrawal, the ATM may sanitize the cash and package the cash within a package (e.g., antiseptic film). In certain embodiments, the ATM may monitor a number of detected uses or of handlings of each bill and based on the number of detected uses or handlings of the bills determine if the bills should be sanitized. In certain embodiments, the ATM may image the bills to confirm the cash amount. In other embodiments, the ATM may inquire of the user if an alternative action may be taken to avoid the cash withdrawal (e.g., arrange a payment to a business or individual through the ATM). In some embodiments, components of the ATM may be sanitized after each use (e.g., sanitization of a user input device such as a keypad or display). By sanitizing the cash and/or components of the ATM, in conjunction with reducing cash transactions, systems and methods in accordance with present embodiments may reduce the transfer of germs and contagions between individuals during transactions with ATMs.

Figure 1:
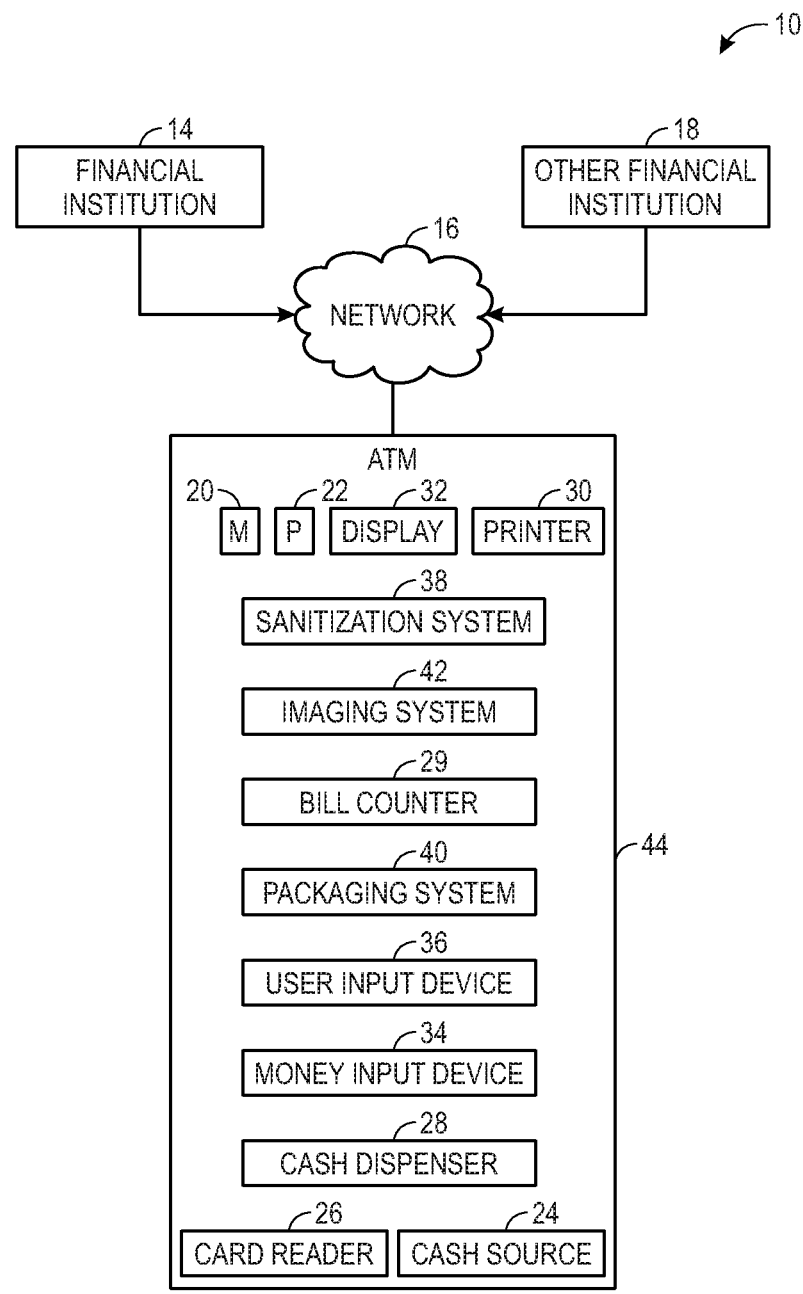
FIG. 1 is a schematic diagram of an embodiment of a system for conducting financial transactions in a sanitary manner, in accordance with an embodiment of the present disclosure.

With this in mind, FIG. 1 is a schematic diagram of an embodiment of a system 10 for conducting financial transactions in a sanitary manner. The system 10 includes an ATM 12 configured to dispense cash to a user in a sanitized manner. The ATM 12 is coupled to the user's financial institution 14 via any suitable communication network or networks 16, including a mobile communication network, a Wi-Fi network, local area network (LAN), wide area network (WAN), and/or the Internet. The ATM 12 may be coupled to other financial institutions 18 (e.g., of different businesses or individuals) via the network 16.

The ATM 12 includes a memory 20 and a processor or processing circuitry 22. The memory 20 may include volatile memory, such as random-access memory (RAM), and/or non-volatile memory, such as read-only memory (ROM), optical drives, hard disc drives, solid-state drives, or any other non-transitory computer-readable medium that includes instructions executable by the processor 22. The processor 22 may include one or more application specific integrated circuits (ASICs), one or more field programmable gate arrays (FPGAs), one or more general purpose processors, or any combination thereof, configured to execute the instructions stored in the memory 20, such as to perform the processes and logic flows described in this specification. It should be noted that the ATM 12 may utilize processing capabilities and memory available from a cloud system.

The ATM 12 also includes a cash source 24 (e.g., reservoirs of various cash bills), a card reader 26 for reading account information on a debit card or credit card, a cash dispenser 28 for receiving and providing cash (e.g., sanitized cash) to a user via an access port, a bill counter 29 for assembling cash and counting cash, a printer 30 for printing a receipt and/or images, a display 32, and one or more money input devices 34 for receiving cash or checks. The ATM 12 also includes a user interface or user input device 36. The user input device 36 may be a keypad, a touchscreen, or other device. If the user input device 36 is a touchscreen it may be part of the display 32 or separate from the display 32. In some embodiments, the user input device 36 includes an interface for securely communicating with a user's personal device (e.g., smart phone) in a manner that allows the user to employ the personal device to provide input (e.g., request a withdrawal and provide a password) to the ATM 12.

The ATM 12 further includes a sanitization system 38. The sanitization system 38 is configured to sanitize the bills before they are dispensed to the user. In certain embodiments, the sanitization system 38 may include an ultraviolet (UV) light source configured to emit UV for a set period of time to sanitize the cash. The sanitization system 38 may also be configured to sanitize the user input device 36 after the user finishes using the ATM 12. In certain embodiments, the sanitization system 38 may include the UV light source to emit UV for a set period of time to sanitize the user input device 36. Additionally or alternatively, the sanitization system 38 may include a sanitizer source for spaying a sanitizer on the user input device 36 or a source for coating an antiviral coating on the user input device 36.

It may be desirable to limit or block exposure to such sanitation procedures (e.g., sanitizing spray, UV light). Thus, for example, the user input device 36 may be disposed within a recess of a housing of the ATM 12, and the recess may be sealed away from the surrounding environment by a door (e.g., a transitional sealing layer) for sanitation purposes between interactions. Specifically, for example, a door may transition from an open position to a closed position to block access to an interior of the recess and such that the user input device 36 is essentially enclosed within the ATM 12 for sanitization to occur via the sanitization system 38. In certain embodiments, the user input device 36 may not be disposed in a recess but on the outer portion of a housing of the ATM 12. In this case, components of the sanitization system 38 may also be disposed on the outer portion of the housing of the ATM 12 to sanitize the user input device 36. In such embodiments, a scrolling or hinged door or cover may be actuated to cover the user input device 36 (e.g., a keypad or communication port) during sanitation. In fact, the door may include the sanitization features (e.g., spray nozzles or UV light bulbs) such that the sanitation features are trained on the input device 36 when the door is in a closed configuration. By enclosing or blocking the input device 36 from external access during sanitation procedures, present embodiments may avoid undesired contact from a user during sanitation and also limit required sanitation times and/or quantities of related material (e.g., sanitizing spray, replacement UV bulbs) by concentrating the sanitation activity in a limited space, which may improve effectiveness.

The ATM 12 also includes a packaging system 40 that operates to seal the sanitized cash in a package before dispersal to the user. In certain embodiments, the packaging system 40 may seal the cash in an antiseptic film made of nanomaterials. In certain embodiments, the package may be transparent or translucent to enable visualization of the cash. In certain embodiments, the cash may be sealed in the package and then the package sanitized via the sanitization system 38. Prior to sealing the case in the package, the cash or bills may be offset from each other (e.g., fanned) to enhance visualization of each bill. Thus, the packaging system 40 may have a bill counting mechanism or bill counter that also arranges the bills in an offset arrangement (e.g., fanned or stepped within a stack) so that each individual bill in the stack can be seen and counted. In some embodiments, this may include each bill being fully visible, wherein a sheet of the bills is formed by sealing the fully exposed bills in a transparent or translucent material. The packaging system 40 may include a dynamic stacking shelf system (e.g., for partially offset stacks) that can adjust into a stepped configuration, air nozzles that provide puffs of air to guide the individual bills into proper alignment as they are dispensed into a stack or arrangement, and/or a vacuum system to pull the bills into desired positions. Further, the packaging system 40 may include a system for stacking the bills on a first layer of sealing material, positioning a second layer of sealing material on a top of the stack, and sealing the two layers together about the stack. In some embodiments, shrink wrapping and a heater for activating the shrink wrapping may be used to tightly seal the stack. Also, in some embodiments, a disinfectant may be sprayed into the package before or after sealing. This may include dispensing disinfectant on to interior surfaces of the packaging material prior to sealing it about the stack.

The ATM 12 further includes an imaging system 42. In certain embodiments, the imaging system 42 may include a camera. The imaging system 42 is configured to image the bills to enable the ATM 12 to verify the amount of cash. In certain embodiments, the image or images may be printed and provided to the user via the printer 30 along with the receipt. The images may also be displayed on the display 32 for the user to verify the amount of cash. This may facilitate confirmation by the user of the desired amount of cash without having to physically tab through the bills. Any discrepancy in the amount listed for receipt and the amount visible to the user in an image of the bills can be indicated via the user input device 36. The ATM 12 may be programmed to automatically address discrepancies or an interface with a customer service representative may be initiated when a user indicates a discrepancy (e.g., a discrepancy above a threshold amount). The imaging system 42 may image the bills prior to sealing within the package (e.g., after being offset) by the packaging system 40 to verify the amount of cash. Alternatively, if the package is transparent or translucent and the bills are offset from each other, the imaging system 42 may image the bills after sealing. Light used to capture the image of the bills may include UV light to improve sanitization. All of the components of the ATM 12 described above are disposed within a housing 44 and/or on an outer portion of the housing 44. One or more of the components may be utilized by the various systems of the ATM 12.

Figure 2:
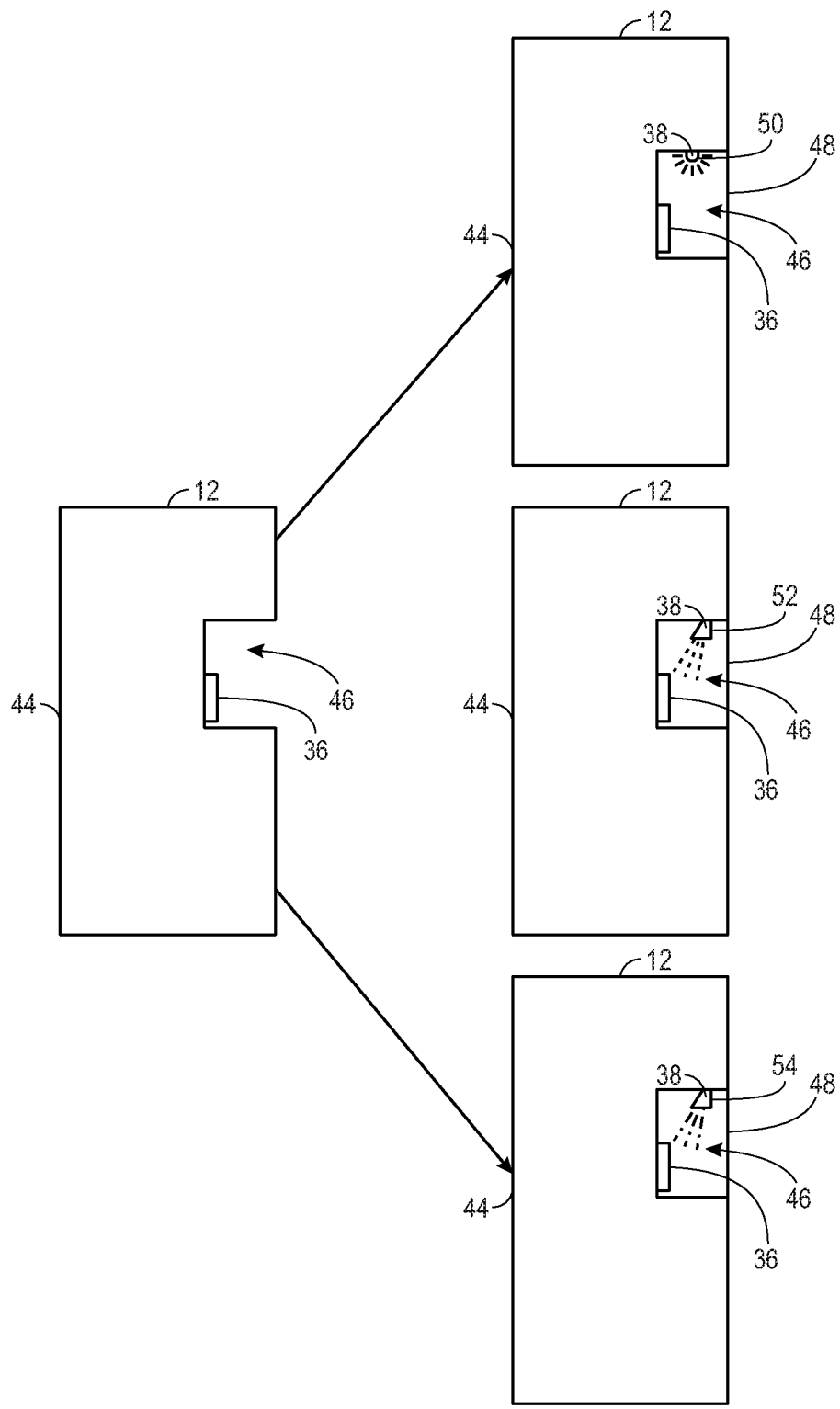
FIG. 2 is a schematic diagram of an embodiment of a user input device of an automated teller machine (ATM) in various stages of a sanitation procedure, in accordance with an embodiment of the present disclosure.

FIG. 2 is a schematic diagram of an embodiment of the user input device 36 of the ATM 12 in various stages of a sanitization process in accordance with the present disclosure. As depicted, the ATM 12 includes the user input device 36 (e.g., keypad or touchscreen) disposed within a recess 46 of the housing 44. During use or awaiting use post-sanitization, the user input device 36 is exposed for utilization by the user. After utilization of the ATM 12 by a user (e.g., after a transaction has been deemed complete), a door 48 closes to enclose the user input device 36 within the recess 46. In certain embodiments, upon closure of the door 48, UV light may be emitted on the user input device 36 for a period of time via a UV light source 50 of the sanitization system 38. In other embodiments, upon closure of the door 48, a sanitizer may be sprayed via a sanitizer source 52 of the sanitization system 38 on the user input device 36. In some embodiments, upon closure of the door 48, an antiviral coating may be coated on the user input device 36 via an antiviral coating source 54 of the sanitization system 38. Upon sanitization of the user input device 36, the door 48 may be opened again. As noted above, in certain embodiments, the user input device 36 may be disposed on an outer portion of housing 44 of the ATM 12 instead of in the recess 46. In this case, components of the sanitization system 38 may also be disposed on the outer portion of the housing 44 of the ATM 12 to sanitize the user input device 36. Further, while the illustrated embodiments show the sanitation sources (e.g., UV light source 50, the sanitizer source 52, and the antiviral coating source 54) as extending from an inner wall of the recess 46, in other embodiments the sanitation sources may be coupled to the door 48. A benefit of having the sanitation sources coupled to the door 48 may include storing/blocking access to the respective sanitation source or sources when the door is closed (e.g., stowed away). In another embodiment, when the door 48 is in an open configuration that allows access to the recess 46, the door may actually block/enclose the sanitation source or sources that are installed on a fixed structure (not the door 48) of the ATM 12. For example, in a closed configuration, the door 48 may seal the UV light source 48 away from the recess 46 such that opening the door 48 provides a dual function of allowing the UV light source 48 to provide light to the area within the recess 48 while also blocking the UV light from the UV light source 48 from extending out of the recess 48.

Figure 3:
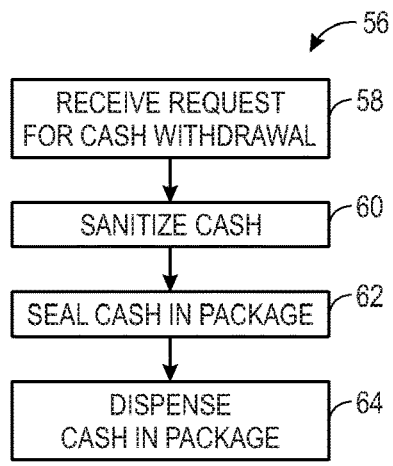
FIG. 3 is a flowchart of an embodiment of a method for dispensing sanitized cash via an ATM, in accordance with an embodiment of the present disclosure.

FIG. 3 is an embodiment of a method 56 for dispensing sanitized cash via the ATM 12. The method 56 may be carried out by one or more components of the ATM 12 of FIG. 1, for example. The method 56 begins with receiving a request for a cash withdrawal from a user (e.g., via the user input device 36) (block 58). The method 56 includes sanitizing one or more bills of cash via the sanitization system 38 (e.g., via UV light) (block 60). The method 56 also includes sealing the bill of cash in a package via the packaging system 40 (block 62). In certain embodiments, the package may be an antiseptic film made of nanomaterials. In certain embodiments, the package may be transparent or translucent to enable visualization of the cash. In some embodiments, the cash may be sealed in the package and then the package sanitized via the sanitization system 38. For example, the package may be exposed to UV light for a time period, wherein the time period may be adjusted based on the amount of cash. This may include injecting sanitizer into the package. The method 64 further includes dispensing the cash in the package via the dispenser 28 (block 64).

Figure 4:
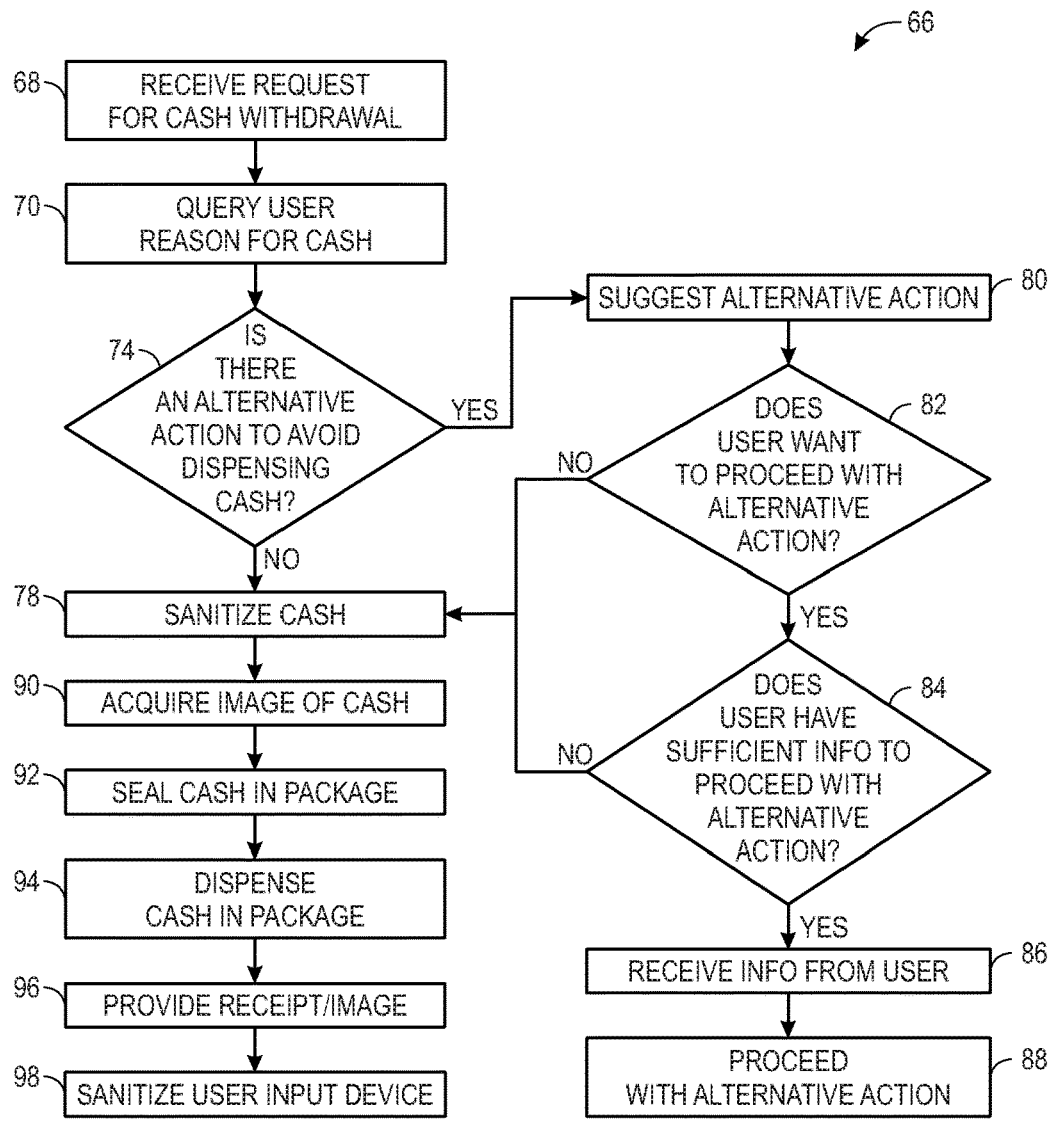
FIG. 4 is a flowchart of an embodiment of a method for dispensing sanitized cash via an ATM, in accordance with an embodiment of the present disclosure.
Figure 5:
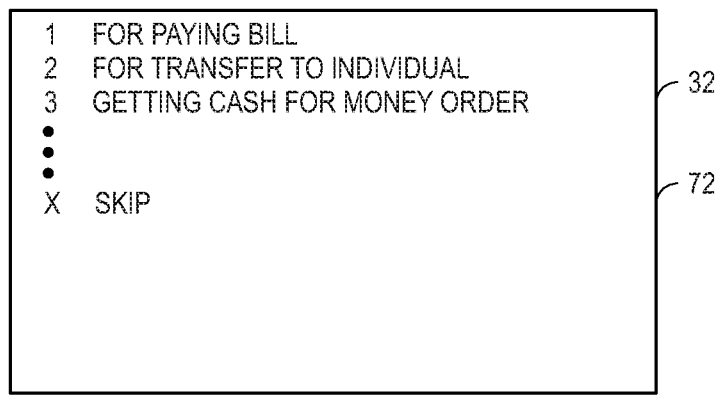
FIG. 5 is an illustration of a screenshot, on a display of an ATM, inquiring about reasons for a cash withdrawal, in accordance with embodiments described herein.

FIG. 4 is an embodiment of another method 66 for dispensing sanitized cash via the ATM 12. The method 66 may be carried out by one or more components of the ATM 12 of FIG. 1, for example. The method 66 begins with receiving a request for a cash withdrawal from a user (e.g., via the user input device 36) (block 68). This may include linking a user device (e.g., a smartphone) to the ATM 12 via the user input device 36. The method 66 includes querying the user as to a reason for the cash withdrawal (block 70). For example, a number of options may be presented on the display 32 for the user to select from using the user input device 36 as depicted in FIG. 5. In some embodiments, the querying may be provided from the ATM 12 to a user device (e.g., smartphone) and displayed thereon. However, FIG. 5 is an example screenshot 72, on the display 32 of the ATM 12. As depicted in the screenshot 72, the options may include various reasons such as paying a bill, for transfer of money to an individual, getting cash for a money order, or any other reason. The screenshot 72 also includes an option for skipping the inquiry if the user does not want to divulge a reason.

In response to a user input providing a reason, the method 66 includes determining whether there is an alternative action to avoid dispensing cash (block 74). If there is not an alternative action (e.g., cash is required for the indicated transaction), then the method 66 proceeds with the ATM 12 sanitizing the cash for the withdrawal (block 78). If there is an alternative action (e.g., an electronic transfer of funds), the method 66 includes suggesting an alternative action to the user (block 80). The alternative actions may include paying the bill, sending a money order or cashier's check, or any other action that avoids having to dispense the cash. Upon suggesting the alternative action, the method 66 includes determining if the user wants to proceed with the suggested alternative action (block 82), which may be determined via a user input. If the user indicates a preference for continuing with a cash withdrawal, then the method 66 proceeds with the ATM 12 sanitizing the cash for the withdrawal (block 78). If the user indicates that the alternative is desired, then the method 66 includes determining whether the user has sufficient information to proceed within the alternative action (block 84). For example, the user may be asked to provide information related to the receiving party (e.g., name, address, account number, etc.). In some embodiments, this may include prompting a receiving party to provide relevant data via certain available data (e.g., an email or local nearfield communication). If the user does not have sufficient information (and contacting the intended recipient cannot address the lacking information), the method 66 proceeds with the ATM 12 sanitizing the cash for the withdrawal (block 78). If sufficient information is available, the method 66 includes receiving the information (e.g., via the user input device 36) (block 86) and proceeding with the suggested alternative action (block 88), which may include mailing a cashier's check, transferring funds electronically, wiring funds, and the like.

In cases where the cash is sanitized (block 78), in certain embodiments, the method 66 includes acquiring an image of the bills of cash via the imaging system 42 (block 90). Imaging the bills enables the ATM 12 to verify the amount of cash. In certain embodiments, the image or images may be printed and provided to the user via the printer 30 along with the receipt. The images may also be displayed on the display 32 for the user to verify the amount of cash. If the amount requested to be withdrawn does not match what is shown, the ATM 12 may provide options for contacting the associated bank or customer service to note the discrepancy and resolve the issue. The imaging system 42 may image the bills prior to sealing within the package (e.g., after being offset) by the packaging system 40 to verify the amount of cash. The method 66 includes sealing the cash in the package (block 92). In certain embodiments, the package may be an antiseptic film made of nanomaterials. In certain embodiments, the package may be transparent or translucent to enable visualization of the cash. In some embodiments, the cash may be sealed in the package and then the package sanitized via the sanitization system 38. Alternatively, if the package is transparent or translucent and the bills are offset from each other, the imaging system 42 may image the bills after sealing.

The method 66 further includes dispensing the cash in the package via the dispenser 28 (block 94). The method 66 includes providing a receipt and/or one or more images of the cash to the user via the printer 30 (block 96). After use of the ATM 12 by the user, the method 66 includes sanitizing the user input device 36 as described above (block 98).

Figure 6:
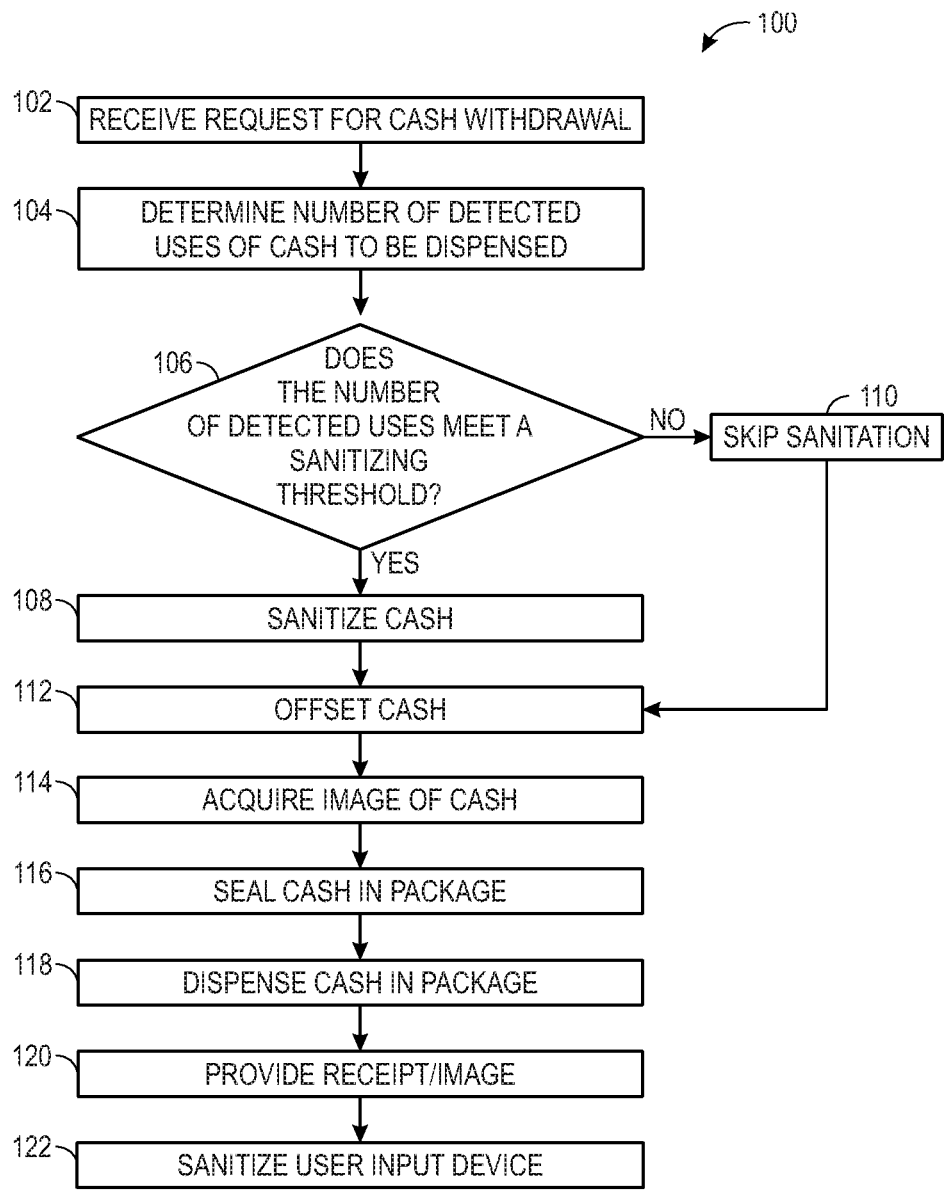
FIG. 6 is a flowchart of an embodiment of a method for dispensing sanitized cash via an ATM, in accordance with an embodiment of the present disclosure.

FIG. 6 is an embodiment of a further method 100 for dispensing sanitized cash via the ATM 12. The method 100 may be carried out by one or more components of the ATM 12 of FIG. 1, for example. The method 100 begins with receiving a request for a cash withdrawal from a user (e.g., via the user input device 36) (block 102). The method 100 includes determining a number of detected uses of each bill of cash to be dispensed (block 104). This may include using machine reading (e.g., optical character recognition) to identify a serial number for the bill and comparing the serial number to a database that stores usage information, such as an indication that the bill with the identified serial number was previously physically deposited at a bank by a small business (e.g., a gas station). Various techniques for tracking bills may be employed and utilized to provide usage information. For example, recently printed bills and their serial numbers may be installed in the ATM and designated as having zero prior usage or not requiring sanitation before being dispensed. Upon determining the number of detected uses, the method 100 includes determining if the number of detected uses meets a sanitizing threshold (e.g., 1, 2, or more uses) (block 106). If the sanitizing threshold is met, the method 100 includes sanitizing one or more of the bills (block 108). In certain embodiments, if one bill of a group of bills to be dispensed needs to be sanitized then all of the bills may be sanitized. In other embodiments only the bill that meets the sanitizing threshold may be sanitized. If the sanitizing threshold is not met, the method 100 includes skipping the sanitization process (block 110).

After sanitization, the method 100 includes offsetting (e.g. fanning) the bills to be dispensed via the packaging system 40 (block 110). In certain embodiments, the method 100 includes acquiring an image of the bills of cash via the imaging system 42 (block 114). Imaging the bills enables the ATM 12 to verify the amount of cash. In certain embodiments, the image or images may be printed and provided to the user via the printer 30 along with the receipt. The images may also be displayed on the display 32 for the user to verify the amount of cash. The imaging system 42 may image the bills prior to sealing within the package (e.g., after being offset) by the packaging system 40 to verify the amount of cash. The method 100 includes sealing the cash in the package (block 116). In certain embodiments, the package may be an antiseptic film made of nanomaterials. In certain embodiments, the package may be transparent or translucent to enable visualization of the cash. In some embodiments, the cash may be sealed in the package and then the package sanitized via the sanitization system 38. Alternatively, if the package is transparent or translucent and the bills are offset from each other, the imaging system 42 may image the bills after sealing.

The method 100 further includes dispensing the cash in the package via the dispenser 28 (block 118). The method 100 includes providing a receipt and/or one or more images of the cash to the user via the printer 30 (block 120). After use of the ATM 12 by the user, the method 100 includes sanitizing the user input device 36 as described above (block 122).

Figure 7:
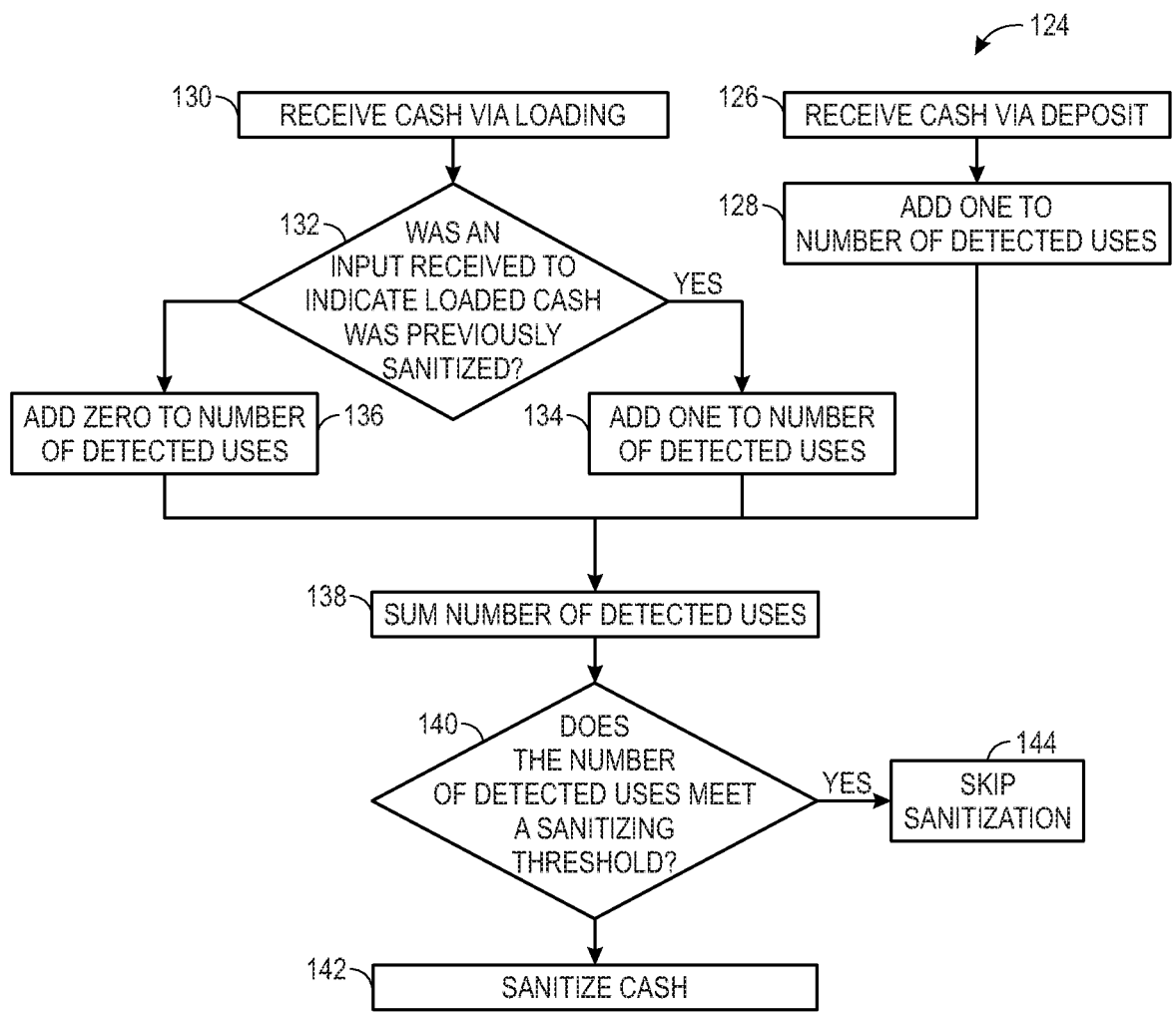
FIG. 7 is a flowchart of an embodiment of a method for determining whether cash should be sanitized via an ATM, in accordance with an embodiment of the present disclosure.

FIG. 7 is an embodiment of a method 124 for determining whether cash should be sanitized via the ATM 12. The method 124 may be carried out by one or more components of the ATM 12 of FIG. 1, for example. The method 124 includes receiving cash via a deposit from a user (block 126). The method 124 also includes adding 1 to the number of detected uses (block 128) since cash received from a user is assumed to be unsanitary.

The method 124 further includes receiving cash via a loading (block 130). Loading is when the ATM 12 is opened up and the cash source 24 is resupplied with bills. The method 124 includes determining whether an input was received from the person that loaded the cash into the ATM 12 indicating the loaded cash was previously sanitized or new right before loading into the ATM 12 (block 132). The person loading the ATM 12 may be able to provide an indication to the ATM 12 that the money is sanitized via the user input device 36 or another mechanism. If no input was received or the input indicated that the loaded money was not sanitized, the method 124 includes adding 1 to the number of detected uses (block 134) since it either known or assumed that the loaded cash is unsanitary. If an input was received that the loaded cash is sanitized, the method 124 includes adding 0 to the number of detected uses (block 136). In some embodiments, identifying usage includes employing machine reading (e.g., optical character recognition) to identify serial numbers and correlate the serial numbers to known historical data in a relevant database.

The method 124 still further includes summing the number of detected uses (block 138) associated with a particular bill (e.g., a serial number for the bill stored in memory). This may include summing detected uses across a network of teller machines and/or uses indicated in a database. The method 124 then includes determining if the number of detected uses meets a sanitizing threshold (e.g., 1, 2, or more uses) (block 140). If the sanitizing threshold is met, the method 124 includes sanitizing one or more of the bills (block 142) via the sanitization system 38 as described above. In certain embodiments, if one bill of a group of bills to be dispensed needs to be sanitized then all of the bills may be sanitized. In other embodiments, only the bill that meets the sanitizing threshold may be sanitized. If the sanitizing threshold is not met, the method 124 includes skipping the sanitization process (block 144).

Figure 8:
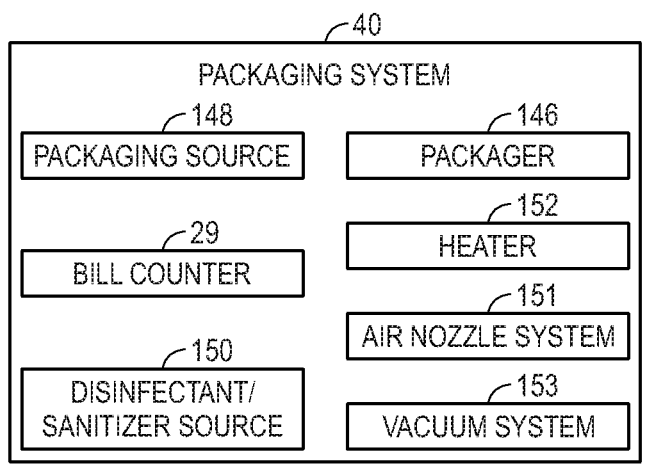
FIG. 8 is schematic diagram of a packaging system of the ATM in FIG. 1, in accordance with an embodiment of the present disclosure.
Figure 9:
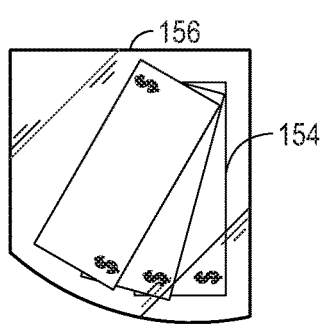
FIG. 9 is a schematic diagram of bills positioned within packaging in a fanned arrangement, in accordance with an embodiment of the present disclosure.
Figure 10:
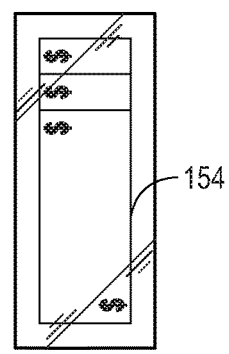
FIG. 10 is a schematic diagram of bills positioned within packaging in a stacked/offset arrangement, in accordance with an embodiment of the present disclosure.
Figure 11:
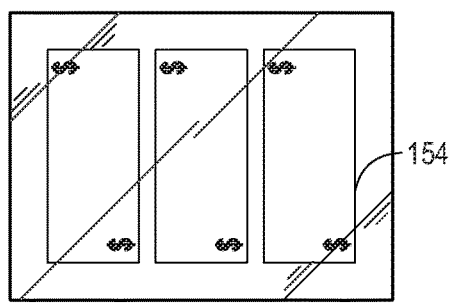
FIG. 11 is a schematic diagram of bills positioned within packaging in a separated arrangement, in accordance with an embodiment of the present disclosure.

FIG. 8 is schematic diagram of the packaging system 40 of the ATM 12 in FIG. 1. The packaging system 40 may include the bill counter 29, a packager 146, a packaging source 148 (e.g., source for shrink wrap or antiseptic film), a disinfectant/sanitizer source 150 for providing a disinfect or sanitizer, a heater 152 for sealing the shrink wrap, an air nozzle system 151 for positioning bills in a proper arrangement, and/or a vacuum system 153 for positioning bills in a proper arrangement. As noted above, the packaging system 40 operates to seal the sanitized cash in a package before dispersal to the user. In certain embodiments, the packaging system 40 may seal the cash in an antiseptic film made of nanomaterials. In certain embodiments, the package may be transparent or translucent to enable visualization of the cash. In certain embodiments, the cash may be sealed in the package and then the package sanitized via the sanitization system 38. Prior to sealing the case in the package, the cash or bills may be offset from each other (e.g., fanned or stepped) to enhance visualization of each bill. Thus, the packaging system 40 may have a bill counting mechanism or bill counter (e.g., bill counter 29) that also arranges the bills in an offset arrangement (e.g., fanned or stepped within a stack) so that each individual bill in the stack can be seen and counted. In some embodiments, this may include each bill being fully visible, wherein a sheet of the bills is formed by sealing the fully exposed bills in a transparent or translucent material. FIGS. 9, 10, and 11 depict examples of bills 154 displayed in a manner to be visible within translucent packaging 156 (e.g., fanned, arrangement, stacked/offset arrangement, or separate arrangement, respectively).

Figure 12:
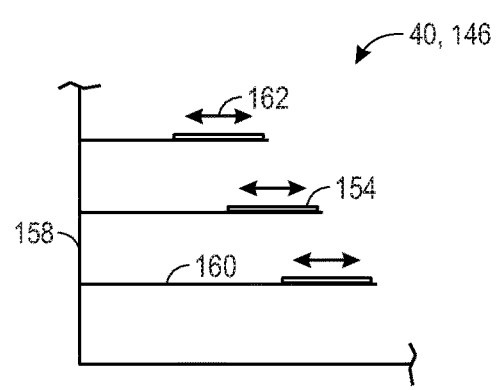
FIG. 12 is a schematic diagram of a dynamic shelfing system for arranging bills, in accordance with an embodiment of the present disclosure.
Figure 13:
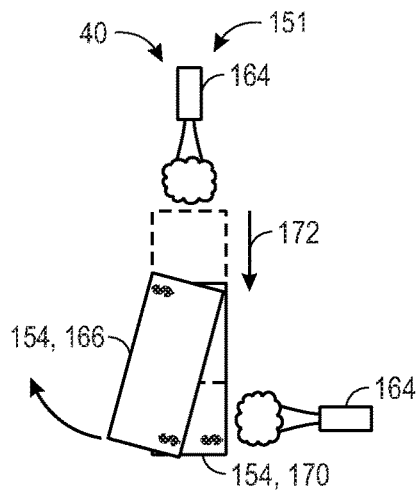
FIG. 13 is a schematic diagram of an air nozzle system for arranging bills, in accordance with an embodiment of the present disclosure.
Figure 14:
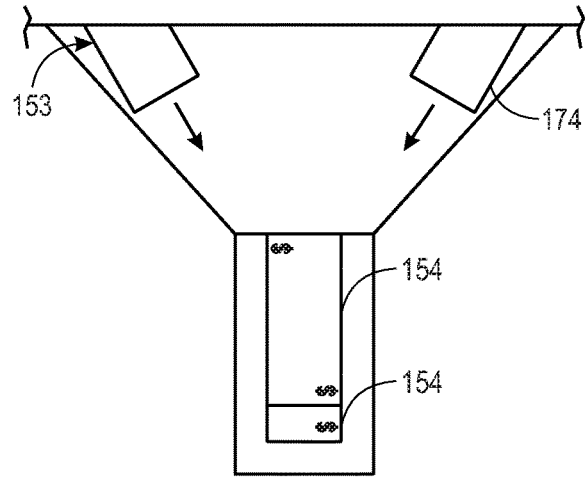
FIG. 14 is a schematic diagram of a vacuum system for arranging bills, in accordance with an embodiment of the present disclosure.

The packaging system 40 (e.g., packager 146) may include a dynamic stacking shelf system 158 (e.g., for partially offset stacks) that includes multiple shelfs 160 that can be adjusted into a stepped configuration as indicated by the arrows 162 in FIG. 12. As noted above, the packaging system 40 may include the air nozzle system 151 (e.g., including one or more air nozzles 164) for that providing puffs of air to guide the individual bills 154 into proper alignment as they are dispensed into a stack or arrangement as depicted in FIG. 13. For example, one air nozzle 164 may move a first bill 166 in a first direction 168 and a second air nozzle may move a second bill 170 in a second direction 172 to achieve a fanned arrangement. The position of the nozzles 164 may be adjustable to achieve the desired arrangement of the bills 154. In addition, as noted above, the packing system 40 may include the vacuum system 53 to pull the bills 154 into desired positions via suction along one or more passages 174 for the bills 154 as depicted in FIG. 14.

Figure 15:
FIG. 15 is a schematic diagram of a bills arranged between different packaging layers, in accordance with an embodiment of the present disclosure.

Further, the packaging system 40 may include a system for stacking the bills 154 on a first layer of sealing material 176, positioning a second layer of sealing material 178 on top of the stack of bills 154, and sealing the two layers 176, 178 together about the stack of bills 154 as depicted in FIG. 15. In some embodiments, shrink-wrapping and the heater 152 for activating the shrink-wrapping may be used to tightly seal the stack. Also, in some embodiments, a disinfectant (e.g., from the source 150) may be sprayed into the package before or after sealing. This may include dispensing disinfectant on to interior surfaces of the packaging material prior to sealing it about the stack.

While only certain features of disclosed embodiments have been illustrated and described herein, many modifications and changes will occur to those skilled in the art. It is, therefore, to be understood that the appended claims are intended to cover all such modifications and changes as fall within the true spirit of the present disclosure.

The techniques presented and claimed herein are referenced and applied to material objects and concrete examples of a practical nature that demonstrably improve the present technical field and, as such, are not abstract, intangible or purely theoretical. Further, if any claims appended to the end of this specification contain one or more elements designated as "means for [perform]ing [a function] . . . " or "step for [perform]ing [a function] . . . ", it is intended that such elements are to be interpreted under 35 U.S.C. 112(f). However, for any claims containing elements designated in any other manner, it is intended that such elements are not to be interpreted under 35 U.S.C. 112(f).

The invention claimed is:
1. An automated teller system, comprising:
a user interface configured to receive user input;
a bill counter configured to assemble cash;
a sanitizer configured to sanitize the cash;
a packager configured to dispose the cash in packaging after the cash has been assembled, wherein the bill counter is configured to offset bills of the cash in a stacked or aligned arrangement prior to the packager sealing the cash in the packaging;

a cash dispenser configured to receive the cash in a sanitized condition and dispense the cash in the sanitized condition via an access port;

one or more processors; and memory storing machine-readable instructions that, when executed by the one or more processors, are configured to cause the one or more processors to:

control the bill counter to assemble the cash based on a withdrawal request, the withdrawal request received as the user input via the user interface;

control sanitization of the cash by the sanitizer to provide the cash in the sanitized condition; and control the cash dispenser to dispense the cash in the sanitized condition via the access port.

2. The automated teller system of claim 1, wherein the packaging comprises an antiseptic film.

3. The automated teller system of claim 1, wherein the sanitizer comprises the packager and is configured to sanitize the cash by sealing the cash in the packaging including transparent or translucent material.

4. The automated teller system of claim 1, wherein the sanitizer is configured to emit ultraviolet light on the cash.

5. The automated teller system of claim 1, wherein the instructions, when executed by the one or more processors, are configured to cause the one or more processors to control a camera to capture an image of the cash prior to dispensing of the cash to enable verification of a cash amount.

6. The automated teller system of claim 1, wherein the instructions, when executed by the one or more processors, are configured to cause the one or more processors to provide a query to the user for a reason for the cash withdrawal and to suggest an alternative action to forego providing the cash to the user based on the reason provided.

7. The automated teller system of claim 1, wherein the sanitizer is configured to sanitize the user interface.

8. The automated teller system of claim 1, wherein the sanitizer is configured to emit ultraviolet light, spray a sanitizer, or provide an antiviral coating.

9. A method for dispensing cash from an automated teller machine (ATM), comprising:

receiving, via a user interface of the ATM, a request for a cash withdrawal from a user;

sanitizing the cash via a sanitizer within a housing of the ATM;

capturing an image of the sanitized cash with a camera within the housing of the ATM prior to dispensing the sanitized cash to the user to enable verification of a cash amount; and providing the sanitized cash to the user via a dispenser of the ATM.

10. The method of claim 9, comprising sealing the sanitized cash within a package by a packager disposed within the housing of the ATM.

11. The method of claim 10, wherein the package comprises an antiseptic film.

12. The method of claim 10, comprising offsetting bills of the sanitized cash prior to the sealing of the sanitized cash within the package.

13. The method of claim 9, comprising determining a number of uses of each bill of the cash and determining whether to initiate the sanitization of the cash based on the determined number of uses.

14. The method of claim 9, comprising querying the user for a reason for the cash withdrawal and suggesting an alternative action to forego providing the cash to the user when the alternative action is available.

15. The method of claim 9, comprising sanitizing of the user interface of the ATM after the user finishes using the ATM.

16. An automated teller system (ATM), comprising:

a user input device configured to enable a user to request a cash withdrawal; and a sanitization machine configured to sanitize cash and to package the sanitized cash within a package prior to providing the cash to the user, wherein the sanitization machine is configured to sanitize the user input device after providing the cash to the user, wherein the package comprises an antiseptic film.

17. An automated teller system, comprising:

a user interface configured to receive user input;

a bill counter configured to assemble cash;

a sanitizer configured to sanitize the cash;

a cash dispenser configured to receive the cash in a sanitized condition and dispense the cash in the sanitized condition via an access port;

one or more processors; and memory storing machine-readable instructions that, when executed by the one or more processors, are configured to cause the one or more processors to:

control the bill counter to assemble the cash based on a withdrawal request, the withdrawal request received as the user input via the user interface;

control sanitization of the cash by the sanitizer to provide the cash in the sanitized condition;

determine a number of uses of each bill of the cash and control the sanitizer based on the determined number of uses; and control the cash dispenser to dispense the cash in the sanitized condition via the access port.

18. An automated teller system, comprising:

a user interface configured to receive user input;

a bill counter configured to assemble cash;

a sanitizer configured to sanitize the cash;

a packager configured to dispose the cash in packaging after the cash has been assembled, wherein the sanitizer comprises the packager and is configured to sanitize the cash by sealing the cash in the packaging including transparent or translucent material;

a cash dispenser configured to receive the cash in a sanitized condition and dispense the cash in the sanitized condition via an access port;

one or more processors; and memory storing machine-readable instructions that, when executed by the one or more processors, are configured to cause the one or more processors to:

control the bill counter to assemble the cash based on a withdrawal request, the withdrawal request received as the user input via the user interface;

control sanitization of the cash by the sanitizer to provide the cash in the sanitized condition; and control the cash dispenser to dispense the cash in the sanitized condition via the access port.

19. An automated teller system, comprising:

a user interface configured to receive user input;

a bill counter configured to assemble cash;

a sanitizer configured to sanitize the cash;

a cash dispenser configured to receive the cash in a sanitized condition and dispense the cash in the sanitized condition via an access port;

one or more processors; and memory storing machine-readable instructions that, when executed by the one or more processors, are configured to cause the one or more processors to:

control the bill counter to assemble the cash based on a cash withdrawal request, the withdrawal request received as the user input via the user interface;

provide a query to the user for a reason for the cash withdrawal request and to suggest an alternative action to forego providing the cash to the user based on the reason provided;

control sanitization of the cash by the sanitizer to provide the cash in the sanitized condition; and control the cash dispenser to dispense the cash in the sanitized condition via the access port.

\* \* \* \* \*